US012799489B2

(12) United States Patent
Haushalter et al.

(10) Patent No.: US 12,799,489 B2
(45) Date of Patent: Nov. 17, 2026

(54) HOST CELLS AND METHODS FOR PRODUCING HYDROXYLATED METHYL KETONE COMPOUNDS

(71) Applicant: The Regents of the University of California, Oakland, CA (US)

(72) Inventors: Robert W. Haushalter, Emeryville, CA (US); Ee-Been Goh, Emeryville, CA (US); Jorge Alonso-Gutierrez, San Francisco, CA (US); Leonard Katz, Oakland, CA (US); Jay D. Keasling, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/383,352

(22) Filed: Jul. 22, 2021

(65) Prior Publication Data

US 2022/0025380 A1 Jan. 27, 2022

Related U.S. Application Data

(60) Provisional application No. 63/055,264, filed on Jul. 22, 2020.

(51) Int. Cl.

| | |
|---|---|
| ***C12N 15/52*** | (2006.01) |
| ***C12N 1/21*** | (2006.01) |
| ***C12N 9/02*** | (2006.01) |
| ***C12N 9/16*** | (2006.01) |
| ***C12P 7/26*** | (2006.01) |

(52) U.S. Cl.

CPC ........... *C12N 15/52* (2013.01); *C12N 9/0071* (2013.01); *C12N 9/16* (2013.01); *C12P 7/26* (2013.01); *C12N 2510/02* (2013.01)

(58) Field of Classification Search

None

See application file for complete search history.

(56) References Cited

U.S. PATENT DOCUMENTS

| | | | | |
|---|---|---|---|---|
| 4,500,707 | A | 2/1985 | Caruthers et al. | |
| 4,683,195 | A | 7/1987 | Mullis et al. | |
| 5,436,327 | A | 7/1995 | Southern et al. | |
| 5,700,637 | A | 12/1997 | Southern | |
| 7,985,567 | B2 | 7/2011 | Chou et al. | |
| 8,420,833 | B2 | 4/2013 | Katz et al. | |
| 8,852,902 | B2 | 10/2014 | Katz et al. | |
| 9,109,175 | B2 | 8/2015 | Lee et al. | |
| 9,200,298 | B2 | 12/2015 | Lee et al. | |
| 9,334,514 | B2 | 5/2016 | Fortman et al. | |
| 9,376,691 | B2 | 6/2016 | Peralta-Yahya et al. | |
| 9,382,553 | B2 | 7/2016 | Kirby et al. | |
| 9,556,458 | B2 * | 1/2017 | Beller | C12N 9/16 |
| 9,631,210 | B2 | 4/2017 | Chou et al. | |
| 9,951,345 | B2 | 4/2018 | Steen et al. | |
| 9,994,881 | B2 * | 6/2018 | Gonzalez | C12P 7/44 |
| 10,167,488 | B2 | 1/2019 | Keasling et al. | |
| 2013/0267012 | A1 | 10/2013 | Steen et al. | |
| 2014/0038850 | A1 * | 2/2014 | Fasan | C12Q 1/26 506/11 |
| 2016/0130616 | A1 * | 5/2016 | Schirmer | C12N 15/52 435/252.31 |
| 2018/0135059 | A1 * | 5/2018 | Gonzalez | A61K 38/00 |

FOREIGN PATENT DOCUMENTS

| | | | |
|---|---|---|---|
| WO | 2009/006386 | A2 | 1/2009 |
| WO | 2009/006429 | A1 | 1/2009 |
| WO | 2009/006430 | A1 | 1/2009 |
| WO | 2009/134899 | A2 | 11/2009 |
| WO | 2010/127318 | A2 | 11/2010 |
| WO | 2012/135389 | A2 | 3/2012 |
| WO | 2012/050931 | A2 | 4/2012 |
| WO | 2012/058686 | A2 | 5/2012 |
| WO | 2012/064740 | A1 | 5/2012 |
| WO | 2012/071439 | A1 | 5/2012 |
| WO | 2014/093402 | A2 | 6/2014 |
| WO | 2015/013674 | A2 | 1/2015 |
| WO | 2017/214159 | A1 | 12/2017 |
| WO | 2018/200888 | A1 | 11/2018 |
| WO | 2019/050990 | A1 | 3/2019 |

OTHER PUBLICATIONS

Peters et al., Regio- and Enantioselective Alkane Hydroxylation with Engineered Cytochromes P450 BM-3, J. Am. Chem. Soc. 125, 2003, 13442-49. (Year: 2003).*

McLean et al., Microbial cytochromes P450, Chapter 6 in Cytochrome P450: Structure, Mechanism, and Biochemistry, 4th Ed., 2015. (Year: 2015).*

Pearson, Effective Protein Sequence Comparison, Methods Enz. 266, 1996, 227-58. (Year: 1996).*

Uniprot, Accession No. Q9K498, 2019, www.uniprot.org. (Year: 2019).*

Zhao et al., Crystal structure of albaflavenone monooxygenase containing a moonlighting terpene synthase active site, J. Biol. Chem., 2009, 36711-19. (Year: 2009).*

Van Bogaert et al., The role of cytochrome P450 monooxygenases in microbial fatty acid metabolism, FEBS J. 278, 2011, 206-21. (Year: 2011).*

Shine et al. "Determinant of cistron specificity in bacterial ribosomes", Nature 254:34 (1975).

Steitz, in Biological Regulation and Development: Gene Expression (ed. R. F. Goldberger), vol. 1, p. 349, 1979.

(Continued)

*Primary Examiner* — Todd M Epstein

(74) *Attorney, Agent, or Firm* — Robin C. Chiang; LAWRENCE BERKELEY NATIONAL LABORATORY

(57) ABSTRACT

This present invention provides a genetically modified host cell, such as an *E. coli* host cell, capable of producing or overproducing a hydroxylated methyl ketone (HMK), such as an omega-hydroxy and/or omega-1-hydroxy methyl ketone.

23 Claims, 7 Drawing Sheets

Specification includes a Sequence Listing.

(56) References Cited

OTHER PUBLICATIONS

DeBoer et al. "The tac promoter: a functional hybrid derived from the trp and lac promoters" Proc. Natl. Acad. Sci. USA, 80:21-25 (1983).
Hammerer, L., et al., 2018. Regioselective biocatalytic hydroxylation of fatty acids by cytochrome P450s. Catalysis Letters, 148, pp. 787-812.
Hardwick, J.P., 2008. Cytochrome P450 omega hydroxylase (CYP4) function in fatty acid metabolism and metabolic diseases. Biochemical pharmacology, 75(12), pp. 2263-2275.
Wang, X., et al., 2012. Biosynthesis of long chain hydroxyfatty acids from glucose by engineered *Escherichia coli*. Bioresource technology, 114, pp. 561-566.
Zhao, B., et al., 2008. Biosynthesis of the sesquiterpene antibiotic albaflavenone in Streptomyces coelicolor A3 (2). Journal of Biological Chemistry, 283(13), pp. 8183-8189.
Zhao, B. et al., 2011. Moonlighting cytochrome P450 monooxygenases. IUBMB life, 63(7), pp. 473-477.

* cited by examiner 1 2 3 4 5 6

13 14 15 16 17 18 19 20 21 22 23 24 25 26 27 28 29 30

13 37

14 38

15 39

16 40

17 41

18 42

19 43

20 44

21 45 x= 1-11

SEQUENCE LISTING

```
<160> NUMBER OF SEQ ID NOS: 4

<210> SEQ ID NO 1
<211> LENGTH: 132
<212> TYPE: PRT
<213> ORGANISM: Escherichia coli

<400> SEQUENCE: 1

Met Gln Thr Gln Ile Lys Val Arg Gly Tyr His Leu Asp Val Tyr Gln
1               5                   10                  15

His Val Asn Asn Ala Arg Tyr Leu Glu Phe Leu Glu Glu Ala Arg Trp
            20                  25                  30

Asp Gly Leu Glu Asn Ser Asp Ser Phe Gln Trp Met Thr Ala His Asn
        35                  40                  45

Ile Ala Phe Val Val Val Asn Ile Asn Ile Asn Tyr Arg Arg Pro Ala
    50                  55                  60

Val Leu Ser Asp Leu Leu Thr Ile Thr Ser Gln Leu Gln Gln Leu Asn
65                  70                  75                  80

Gly Lys Ser Gly Ile Leu Ser Gln Val Ile Thr Leu Glu Pro Glu Gly
                85                  90                  95

Gln Val Val Ala Asp Ala Leu Ile Thr Phe Val Cys Ile Asp Leu Lys
            100                 105                 110

Thr Gln Lys Ala Leu Ala Leu Glu Gly Glu Leu Arg Glu Lys Leu Glu
        115                 120                 125

Gln Met Val Lys
```

130

<210> SEQ ID NO 2
<211> LENGTH: 707
<212> TYPE: PRT
<213> ORGANISM: Micrococcus luteus

<400> SEQUENCE: 2

```
Met Thr Val His Glu Lys Leu Ala Pro Gln Ser Pro Thr His Ser Thr
1               5                   10                  15

Glu Val Pro Thr Asp Val Ala Glu Ile Ala Pro Glu Arg Pro Thr Pro
            20                  25                  30

Gly Ser Leu Asp Ala Ala Ala Leu Glu Glu Ala Leu Leu Gly Arg Trp
        35                  40                  45

Ala Ala Glu Arg Arg Glu Ser Arg Glu Leu Ala Lys Asp Pro Ala Leu
    50                  55                  60

Trp Arg Asp Pro Leu Leu Gly Met Asp Glu His Arg Ala Arg Val Leu
65                  70                  75                  80

Arg Gln Leu Gly Val Leu Val Glu Arg Asn Ala Val His Arg Ala Phe
                85                  90                  95

Pro Arg Glu Phe Gly Gly Glu Asp Asn His Gly Gly Asn Ile Ser Ala
            100                 105                 110

Phe Gly Asp Leu Val Leu Ala Asp Pro Ser Leu Gln Ile Lys Ala Gly
        115                 120                 125

Val Gln Trp Gly Leu Phe Ser Ser Ala Ile Leu His Leu Gly Thr Ala
    130                 135                 140

Glu His His Arg Arg Trp Leu Pro Gly Ala Met Asp Leu Ser Val Pro
145                 150                 155                 160

Gly Ala Phe Ala Met Thr Glu Ile Gly His Gly Ser Asp Val Ala Ser
                165                 170                 175

Ile Ala Thr Thr Ala Thr Tyr Asp Glu Ala Thr Gln Glu Phe Val Ile
            180                 185                 190

His Thr Pro Phe Lys Gly Ala Trp Lys Asp Tyr Leu Gly Asn Ala Ala
        195                 200                 205

Leu His Gly Arg Ala Ala Thr Val Phe Ala Gln Leu Ile Thr Gln Gly
    210                 215                 220

Val Asn His Gly Val His Cys Phe Tyr Val Pro Ile Arg Asp Glu Lys
225                 230                 235                 240

Gly Ala Phe Leu Pro Gly Val Gly Gly Glu Asp Asp Gly Leu Lys Gly
                245                 250                 255

Gly Leu Asn Gly Ile Asp Asn Gly Arg Leu His Phe Thr Gln Val Arg
            260                 265                 270

Ile Pro Arg Thr Asn Leu Leu Asn Arg Tyr Gly Asp Val Ala Glu Asp
        275                 280                 285

Gly Thr Tyr Ser Ser Pro Ile Ala Ser Pro Gly Arg Arg Phe Phe Thr
    290                 295                 300

Met Leu Gly Thr Leu Val Gln Gly Arg Val Ser Leu Ser Leu Ala Ala
305                 310                 315                 320

Thr Thr Ala Ser Phe Leu Gly Leu His Gly Ala Leu Ala Tyr Ala Glu
                325                 330                 335

Gln Arg Arg Gln Phe Asn Ala Ser Asp Pro Gln Arg Glu Glu Val Leu
            340                 345                 350

Leu Asp Tyr Gln Asn His Gln Arg Arg Leu Ile Asp Arg Leu Ala Arg
        355                 360                 365
```

```
Ala Tyr Ala Asp Ala Phe Ala Ser Asn Glu Leu Val Val Lys Phe Asp
    370                 375                 380

Asp Val Phe Ser Gly Arg Ser Asp Thr Asp Val Asp Arg Gln Glu Leu
385                 390                 395                 400

Glu Thr Leu Ala Ala Ala Val Lys Pro Leu Thr Thr Trp His Ala Leu
                405                 410                 415

Asp Thr Leu Gln Glu Ala Arg Glu Ala Cys Gly Gly Ala Gly Phe Leu
            420                 425                 430

Ala Glu Asn Arg Val Thr Gln Met Arg Ala Asp Leu Asp Val Tyr Val
        435                 440                 445

Thr Phe Glu Gly Asp Asn Thr Val Leu Leu Gln Leu Val Gly Lys Arg
    450                 455                 460

Leu Leu Thr Asp Tyr Ser Lys Glu Phe Gly Arg Leu Asn Val Gly Ala
465                 470                 475                 480

Val Ser Arg Tyr Val Val His Gln Ala Ser Asp Ala Ile His Arg Ala
                485                 490                 495

Gly Leu His Lys Ala Val Gln Ser Val Ala Asp Gly Gly Ser Glu Arg
            500                 505                 510

Arg Ser Ala Asn Trp Phe Lys Asp Pro Ala Val Gln His Glu Leu Leu
        515                 520                 525

Thr Glu Arg Val Arg Ala Lys Thr Ala Asp Val Ala Gly Thr Leu Ser
    530                 535                 540

Gly Ala Arg Gly Lys Gly Gln Ala Ala Gln Ala Glu Ala Phe Asn Thr
545                 550                 555                 560

Arg Gln His Glu Leu Ile Glu Ala Ala Arg Asn His Gly Glu Leu Leu
                565                 570                 575

Gln Trp Glu Ala Phe Thr Arg Ala Leu Glu Gly Ile Thr Asp Glu Thr
            580                 585                 590

Thr Lys Thr Val Leu Thr Trp Leu Arg Asp Leu Phe Ala Leu Arg Leu
        595                 600                 605

Ile Glu Asp Asp Leu Gly Trp Phe Val Ala His Gly Arg Val Ser Ser
    610                 615                 620

Gln Arg Ala Arg Ala Leu Arg Gly Tyr Val Asn Arg Leu Ala Glu Arg
625                 630                 635                 640

Leu Arg Pro Phe Ala Leu Glu Leu Val Glu Ala Phe Gly Leu Glu Pro
                645                 650                 655

Glu His Leu Arg Met Ala Val Ala Thr Asp Ala Glu Thr Gln Arg Gln
            660                 665                 670

Glu Glu Ala His Ala Trp Phe Thr Ala Arg Arg Ala Ala Gly Glu Glu
        675                 680                 685

Pro Glu Asp Glu Lys Ala Val Arg Ala Arg Glu Lys Ala Ala Arg Gly
    690                 695                 700

Arg Arg Gly
705


<210> SEQ ID NO 3
<211> LENGTH: 461
<212> TYPE: PRT
<213> ORGANISM: Streptomyces coelicolor

<400> SEQUENCE: 3

Met Thr Val Glu Ser Val Asn Pro Glu Thr Arg Ala Pro Ala Ala Pro
1               5                   10                  15

Gly Ala Pro Glu Leu Arg Glu Pro Pro Val Ala Gly Gly Gly Val Pro
            20                  25                  30
```

-continued

```
Leu Leu Gly His Gly Trp Arg Leu Ala Arg Asp Pro Leu Ala Phe Met
        35                  40                  45

Ser Gln Leu Arg Asp His Gly Asp Val Val Arg Ile Lys Leu Gly Pro
    50                  55                  60

Lys Thr Val Tyr Ala Val Thr Asn Pro Glu Leu Thr Gly Ala Leu Ala
65                  70                  75                  80

Leu Asn Pro Asp Tyr His Ile Ala Gly Pro Leu Trp Glu Ser Leu Glu
                85                  90                  95

Gly Leu Leu Gly Lys Glu Gly Val Ala Thr Ala Asn Gly Pro Leu His
            100                 105                 110

Arg Arg Gln Arg Arg Thr Ile Gln Pro Ala Phe Arg Leu Asp Ala Ile
        115                 120                 125

Pro Ala Tyr Gly Pro Ile Met Glu Glu Glu Ala His Ala Leu Thr Glu
    130                 135                 140

Arg Trp Gln Pro Gly Lys Thr Val Asp Ala Thr Ser Glu Ser Phe Arg
145                 150                 155                 160

Val Ala Val Arg Val Ala Ala Arg Cys Leu Leu Arg Gly Gln Tyr Met
                165                 170                 175

Asp Glu Arg Ala Glu Arg Leu Cys Val Ala Leu Ala Thr Val Phe Arg
            180                 185                 190

Gly Met Tyr Arg Arg Met Val Val Pro Leu Gly Pro Leu Tyr Arg Leu
        195                 200                 205

Pro Leu Pro Ala Asn Arg Arg Phe Asn Asp Ala Leu Ala Asp Leu His
    210                 215                 220

Leu Leu Val Asp Glu Ile Ile Ala Glu Arg Arg Ala Ser Gly Gln Lys
225                 230                 235                 240

Pro Asp Asp Leu Leu Thr Ala Leu Leu Glu Ala Lys Asp Asp Asn Gly
                245                 250                 255

Asp Pro Ile Gly Glu Gln Glu Ile His Asp Gln Val Val Ala Ile Leu
            260                 265                 270

Thr Pro Gly Ser Glu Thr Ile Ala Ser Thr Ile Met Trp Leu Leu Gln
        275                 280                 285

Ala Leu Ala Asp His Pro Glu His Ala Asp Arg Ile Arg Asp Glu Val
    290                 295                 300

Glu Ala Val Thr Gly Gly Arg Pro Val Ala Phe Glu Asp Val Arg Lys
305                 310                 315                 320

Leu Arg His Thr Gly Asn Val Ile Val Glu Ala Met Arg Leu Arg Pro
                325                 330                 335

Ala Val Trp Val Leu Thr Arg Arg Ala Val Ala Glu Ser Glu Leu Gly
            340                 345                 350

Gly Tyr Arg Ile Pro Ala Gly Ala Asp Ile Ile Tyr Ser Pro Tyr Ala
        355                 360                 365

Ile Gln Arg Asp Pro Lys Ser Tyr Asp Asp Asn Leu Glu Phe Asp Pro
    370                 375                 380

Asp Arg Trp Leu Pro Glu Arg Ala Ala Asn Val Pro Lys Tyr Ala Met
385                 390                 395                 400

Lys Pro Phe Ser Ala Gly Lys Arg Lys Cys Pro Ser Asp His Phe Ser
                405                 410                 415

Met Ala Gln Leu Thr Leu Ile Thr Ala Ala Leu Ala Thr Lys Tyr Arg
            420                 425                 430

Phe Glu Gln Val Ala Gly Ser Asn Asp Ala Val Arg Val Gly Ile Thr
        435                 440                 445
```

-continued

```
Leu Arg Pro His Asp Leu Leu Val Arg Pro Val Ala Arg
    450                 455                 460


<210> SEQ ID NO 4
<211> LENGTH: 8
<212> TYPE: PRT
<213> ORGANISM: Streptomyces coelicolor
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 4

Phe Xaa Xaa Gly Xaa Arg Xaa Cys
1               5
```

HOST CELLS AND METHODS FOR PRODUCING HYDROXYLATED METHYL KETONE COMPOUNDS

CROSS-REFERENCE TO RELATED APPLICATIONS

This application claims priority to U.S. Provisional Patent Application Ser. No. 63/055,264, filed on Jul. 22, 2020, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

REFERENCE TO SEQUENCE LISTING

The instant application contains a Sequence Listing which has been submitted electronically in ASCII text format and is hereby incorporated by reference in its entirety. Said ASCII text copy, created on Oct. 27, 2021, is named “2015-141-02_ST25.txt” and 12 kilobytes in size.

FIELD OF THE INVENTION

This invention relates generally to hydroxylated methyl ketone production.

BACKGROUND OF THE INVENTION

Methyl ketones have a variety of important natural and commercial roles, including acting as pheromones and natural insecticides in plants, or providing scents in essential oils and flavoring in cheese and other dairy products. Biosynthesis of methyl ketones has been hypothesized to derive from a variety of different biological pathways such as fatty acid β-oxidation or aerobic alkene/alkane degradation. These compounds could be relevant to the biofuel industry as well as the flavor and fragrance industry by virtue of their highly reduced, aliphatic character. Indeed, a range of other fatty-acid derived compounds have already been successfully synthesized from metabolically engineered microbes for use as biofuels, such as fatty acid ethyl esters, alkanes, alkenes, and n-alcohols.

U.S. Pat. No. 9,556,458 discloses an engineered pathway to convert fatty acids to methyl ketones in *E. coli* DH1 (see FIG. 1).

SUMMARY OF THE INVENTION

This present invention provides a genetically modified host cell, such as an *E. coli* host cell, capable of producing or overproducing a hydroxylated methyl ketone (HMK), such as an omega-hydroxy and/or omega-1-hydroxy methyl ketone. HMKs, such as omega-hydroxy and omega-1-hydroxy methyl ketones, have potential application in biofuel production and in the flavor and aroma industries.

In some embodiments, the HMK is a branched HMK (BHMK). In some embodiments, the HMK is a saturated HMK (SHMK) or unsaturated HMK (UHMK), such as a monosaturated HMK. In some embodiments, the HMK is a saturated branched HMK (SBHMK). In some embodiments, the HMK is an unsaturated branched HMK (UBHMK).

This present invention provides a genetically modified host cell that produces a hydroxylated methyl ketone (HMK), such as an omega-hydroxy and/or omega-1-hydroxy methyl ketone, wherein the genetically modified host cell comprises: (a) a recombinant nucleic acid construct encoding a cytochrome P450 (CYP) enzyme (or homologous enzyme thereof) that is capable of converting a fatty acid to a HMK, and overproduces fatty acid compared to a control host cell that has not been transformed with the nucleic acid construct encoding the CYP, wherein the CYP comprises an amino acid sequence having at least 60% identity to SEQ ID NO:3; (b) a recombinant nucleic acid construct encoding a FadM (or homologous enzyme thereof) that is capable of converting a β-ketoacyl-CoA to a β-keto acid, and overproduces β-ketoacyl-CoAs compared to a control bacterial host cell that has not been transformed with the nucleic acid construct encoding the FadM, wherein the FadM comprises an amino acid sequence having at least 60% identity to SEQ ID NO:1; (c) a recombinant nucleic acid sequence that encodes an acyl-CoA oxidase (or homologous enzyme thereof) capable of converting an acyl-CoA to a trans-2-enoyl-CoA; comprises a recombinant nucleic acid sequence that encodes a FadB capable of converting a trans-2-enoyl-CoA to a β-hydroxyacyl-CoA and a β-hydroxyacyl-CoA to a β-ketoacyl-CoA; and (d) has an inactive fadA gene or chromosomal deletion of all or part of the fadA gene such that the host cell does not express active FadA.

In some embodiments, the cytochrome P450 (CYP) enzyme is any CYP capable of incorporating omega-, omega-1(R), or omega-1(S) hydroxyl groups in a fatty acids to give a HFA (as described in Example 1 herein). CYPs are a superfamily of enzymes containing heme as a cofactor that function as a monooxygenase. More than 300,000 distinct CYP proteins are known. In some embodiments, the cytochrome P450 (CYP) enzyme is a bacterial CYP.

In some embodiments, the CYP is an epi-isozizaene 5-monooxygenase, such as *Streptomyces coelicolor* epi-isozizaene 5-monooxygenase (CYP170A1). In some embodiments, the CYP enzyme comprises an amino acid sequence having at least 70%, 80%, 90%, 95%, or 99% identity with SEQ ID NO:3.

The amino acid sequence of CYP170A1 is as follows:

(SEQ ID NO: 3)

| | | | |
|---|---|---|---|
| 10 | 20 | 30 | 40 |
| MTVESVNPET | RAPAAPGAPE | LREPPVAGGG | VPLLGHGWRL |
| 50 | 60 | 70 | 80 |
| ARDPLAFMSQ | LRDHGDVVRI | KLGPKTVYAV | TNPELTGALA |
| 90 | 100 | 110 | 120 |
| LNPDYHIAGP | LWESLEGLLG | KEGVATANGP | LHRRQRRTIQ |
| 130 | 140 | 150 | 160 |
| PAFRLDAIPA | YGPIMEEEAH | ALTERWQPGK | TVDATSESFR |
| 170 | 180 | 190 | 200 |
| VAVRVAARCL | LRGQYMDERA | ERLCVALATV | FRGMYRRMVV |
| 210 | 220 | 230 | 240 |
| PLGPLYRLPL | PANRRFNDAL | ADLHLLVDEI | IAERRASGQK |
| 250 | 260 | 270 | 280 |
| PDDLLTALLE | AKDDNGDPIG | EQEIHDQVVA | ILTPGSETIA |
| 290 | 300 | 310 | 320 |
| STIMWLLQAL | ADHPEHADRI | RDEVEAVTGG | RPVAFEDVRK |
| 330 | 340 | 350 | 360 |

-continued

```
LRHTGNVIVE  AMRLRPAVWV  LTRRAVAESE  LGGYRIPAGA

       370         380         390         400
DIIYSPYAIQ  RDPKSYDDNL  EFDPDRWLPE  RAANVPKYAM

       410         420         430         440
KPFSAGKRKC  PSDHFSMAQL  TLITAALATK  YRFEQVAGSN

       450         460
DAVRVGITLR  PHDLLVRPVA  R
```

In some embodiments, the CYP enzyme, or (or homologous enzyme thereof) thereof, comprises FXXGXRXC (SEQ ID NO:4), which forms part of the heme-binding domain and is important for heme-binding, and/or EXXR which forms part of the K-helix which are important for stabilizing the core and heme-binding, wherein X is any naturally occurring amino acid. In some embodiments, the CYP enzyme comprises the amino acid sequence Glu-Xaa-Xaa-Arg (EXXR) motif, wherein Xaa is any naturally occurring amino acid.

In some embodiments, the FadM has at least 70%, 80%, 90%, 95%, or 99% amino acid sequence identity to SEQ ID NO:1. In some embodiments, the FadM is an *Escherichia coli* FadM.

The amino acid sequence of *E. coli* FadM is as follows:

```
                                   (SEQ ID NO: 1)
        10          20          30          40
MQTQIKVRGY  HLDVYQHVNN  ARYLEFLEEA  RWDGLENSDS

        50          60          70          80
FQWMTAHNIA  FVVVNININY  RRPAVLSDLL  TITSQLQQLN

        90         100         110         120
GKSGILSQVI  TLEPEGQVVA  DALITFVCID  LKTQKALALE

       130
GELREKLEQM  VK
```

In some embodiments, the acyl-CoA oxidase has at least 70%, 80%, 90%, 95%, or 99% amino acid sequence identity to SEQ ID NO:2. In some embodiments, the acyl-CoA oxidase is from *Micrococcus luteus.*

The amino acid sequence of *Micrococcus luteus* acyl-CoA oxidase is as follows:

```
                                   (SEQ ID NO: 2)
        10          20          30          40
MTVHEKLAPQ  SPTHSTEVPT  DVAEIAPERP  TPGSLDAAAL

        50          60          70          80
EEALLGRWAA  ERRESRELAK  DPALWRDPLL  GMDEHRARVL

        90         100         110         120
RQLGVLVERN  AVHRAFPREF  GGEDNHGGNI  SAFGDLVLAD

       130         140         150         160
PSLQIKAGVQ  WGLFSSAILH  LGTAEHHRRW  LPGAMDLSVP

       170         180         190         200
GAFAMTEIGH  GSDVASIATT  ATYDEATQEF  VIHTPFKGAW

       210         220         230         240
KDYLGNAALH  GRAATVFAQL  ITQGVNHGVH  CFYVPIRDEK

       250         260         270         280
GAFLPGVGGE  DDGLKGGLNG  IDNGRLHFTQ  VRIPRTNLLN

       290         300         310         320
RYGDVAEDGT  YSSPIASPGR  RFFTMLGTLV  QGRVSLSLAA

       330         340         350         360
```

-continued

```
TTASFLGLHG  ALAYAEQRRQ  FNASDPQREE  VLLDYQNHQR

       370         380         390         400
RLIDRLARAY  ADAFASNELV  VKFDDVFSGR  SDTDVDRQEL

       410         420         430         440
ETLAAAVKPL  TTWHALDTLQ  EAREACGGAG  FLAENRVTQM

       450         460         470         480
RADLDVYVTF  EGDNTVLLQL  VGKRLLTDYS  KEFGRLNVGA

       490         500         510         520
VSRYVVHQAS  DAIHRAGLHK  AVQSVADGGS  ERRSANWFKD

       530         540         550         560
PAVQHELLTE  RVRAKTADVA  GTLSGARGKG  QAAQAEAFNT

       570         580         590         600
RQHELIEAAR  NHGELLQWEA  FTRALEGITD  ETTKTVLTWL

       610         620         630         640
RDLFALRLIE  DDLGWFVAHG  RVSSQRARAL  RGYVNRLAER

       650         660         670         680
LRPFALELVE  AFGLEPEHLR  MAVATDAETQ  RQEEAHAWFT

       690         700
ARRAAGEEPE  DEKAVRAREK  AARGRRG
```

In some embodiments, the genetically modified host cell further comprises a recombinant nucleic acid sequence that encodes a cytoplasmically-directed thioesterase (encoded by the 'tesA gene) (or homologous enzyme thereof). In some embodiments, the cytosolic thiosterase or 'TesA can be cloned using the methods taught in U.S. Patent Application Publication No. 2013/0267012, which is hereby incorporated by reference.

In some embodiments, the genetically modified host cell has an inactive fadE gene or chromosomal deletion of all or part of the fadE gene such that the host cell does not express active FadE. In some embodiments, the genetically modified host cell is deleted or knocked out for an endogenous or native active acyl-coenzyme A dehydrogenase or FadE.

In some embodiments, the genetically modified host cell has an inactive fadA gene or chromosomal deletion of all or part of the fadA gene such that the host cell does not express active FadA. In some embodiments, the genetically modified host cell is deleted or knocked out for an endogenous or native active 3-ketoacyl-CoA thiolase or FadA.

In some embodiments, the genetically modified host cell has an inactive poxB gene or chromosomal deletion of all or part of the poxB gene such that the host cell does not express PoxB.

In some embodiments, the host cell further comprises a recombinant nucleic acid sequence that is capable of expressing FadR or fatty acid metabolism regulator protein (or homologous enzyme thereof), a recombinant nucleic acid sequence that is capable of expressing FadD or a long-chain-fatty-acid-CoA ligase (or homologous enzyme thereof), a recombinant nucleic acid sequence that is capable of expressing FadB or a fatty acid oxidation complex subunit alpha (or homologous enzyme thereof), and/or a recombinant nucleic acid sequence that is capable of expressing FadM or a long-chain acyl-CoA thioesterase (or homologous enzyme thereof).

In some embodiments, the host cell further comprises a recombinant nucleic acid sequence that is capable of expressing FadD or a long-chain-fatty-acid-CoA ligase (or homologous enzyme thereof), a recombinant nucleic acid sequence that is capable of expressing FadB or a fatty acid oxidation complex subunit alpha (or homologous enzyme thereof), and a recombinant nucleic acid sequence that is capable of expressing FadM or a long-chain acyl-CoA thioesterase (or homologous enzyme thereof).

The present invention provides for a method of enhancing production of methyl ketones, the method comprising culturing the genetically modified host cell of the present invention under conditions such that the culturing results in the production of a HMK, such as an omega-hydroxy and/or omega-1-hydroxy methyl ketone.

In some embodiments, the method further comprises recovering the omega-hydroxy and/or omega-1-hydroxy methyl ketone, such as using a decane overlay.

In some embodiments, the method further comprises converting the omega-hydroxy and/or omega-1-hydroxy methyl ketone into a macrocyclic ketone (MCK). In some embodiments, the converting step comprises contacting the HMK, such as an omega-hydroxy and/or omega-1-hydroxy methyl ketone, with a leaving group (LG) halide. In some embodiments, the LG is a tosyl group or a mesyl group. In some embodiments, the halide is a fluoride, chloride, or bromide.

In some embodiments, the engineered host cells overexpresses or expresses an acyl-AACP thioesterase ('TesA), acyl-CoA synthetase (FadD), acyl-CoA oxidase, acyl-CoA hydroxylase/dehydrogenase FadB, acyl-CoA thioesterase FadM, and a bacterial cytochrome P450 (CYP) enzyme; and deleted for FadE and FadA. In some embodiments, the engineered host cells overexpresses or expresses an acyl-AACP thioesterase ('TesA), *Bacillus subtillis* 3-keto-acyl-ACP synthase (FabH), and the enzymes of the *B. subtillis* branched-chain alpha-keto acid dehydrogenase (BKD) pathway; and deleted for FadE.

The recombinant cells that produce HMKs do so through either one of the following, or both of the following processes: In Process 1, the cells produce free fatty acids by overproducing the acyl-ACP thioesterase 'TesA and removing the enzyme FadE, which participates in the degradation of fatty acids. The fatty acids produced are a combination of saturated and unsaturated fatty acids (FIG. 2). These free fatty acids are converted to methyl ketones (MKs) by overproducing the acyl-CoA synthetase FadD, the acyl-CoA oxidase Mlut_11700, the acyl-CoA hydroxylase/dehydrogenase FadB, and the acyl-CoA thioesterase FadM combined with removal of the 3-keto-acyl-CoA thiolase FadA. In process 1, endogenously produced MKs are subsequently converted to HMKs by overproducing a bacterial cytochrome P450 (CYP) enzyme. Different CYP enzymes can install hydroxyl groups at the omega position, or at the omega-1 position with either R- or S-stereochemistry into saturated or unsaturated MKs, yielding the library of HMK compounds 1-6 (FIG. 3).

The present invention also provides for a method comprising introducing a leaving group (LG) to an HMK or SBHMK whereby the HMK or SBHMK cyclizes into an MCK, and introducing a strong base. The strong base is a base strong enough to deprotonate the methyl group adjacent to the ketone to produce an enolate species, such as lithium diisopropyl amide (LDA).

First, the hydroxyl group is derivatized to a reactive leaving group, thus converting the hydroxyl-bound carbon into a electrophile. There are several inexpensive, commercially available chemical reagents for derivatizing hydroxyl groups, including, but not limited to, mesyl chloride and tosyl chloride. Leaving groups are denoted generally as "LG" in FIG. 5. After the hydroxyl group is derivatized to a good leaving group, the compounds are treated with a very strong, sterically hindered base, such as lithium diisopropyl amide (LDA). LDA deprotonates the methyl group adjacent to the ketone and yields an enolate species. The enolate group then displaces the derivatized hydroxyl group through and $S_N2$ nucleophilic attack, creating a C—C bond and yielding a macrocyclic ketone (FIG. 4). Depending on the presence or absence of double bonds in the hydrocarbon chain, and depending on the stereo- and regiospecificity of hydroxylation, HMKs 1-6 are converted to MCKs 31-36 using this process.

Using this same two-step, one-pot chemical process, HMKs 13-21 can be converted to MCKs 37-45 (FIG. 6).

Similarly, unsaturated HMKs 22-30 can be converted to MCKs 46-54 (FIG. 7).

The invention comprises novel processes for producing, and recombinant cells that produce, hydroxylated methyl ketones (HMKs) from glucose, as well as the compositions of several novel compounds and the process for converting these HMKs into macrocyclic ketones (MCKs), many of which are high value fragrance compounds. The invention provides a means of producing several previously uncharacterized compounds that are structurally related to high value fragrance molecules and could be investigated as novel fragrance compounds.

The recombinant cells that produce HMKs do so through either one of the following, or both of the following processes: In Process 1, the cells produce free fatty acids by overproducing the acyl-ACP thioesterase 'TesA and removing the enzyme FadE, which participates in the degradation of fatty acids. The fatty acids produced are a combination of saturated and unsaturated fatty acids (FIG. 2). These free fatty acids are converted to methyl ketones (MKs) by overproducing the acyl-CoA synthetase FadD, the acyl-CoA oxidase Mlut_11700, the acyl-CoA hydroxylase/dehydrogenase FadB, and the acyl-CoA thioesterase FadM combined with removal of the 3-keto-acyl-CoA thiolase FadA. In process 1, endogenously produced MKs are subsequently converted to HMKs by overproducing a bacterial cytochrome P450 (CYP) enzyme. Different CYP enzymes can install hydroxyl groups at the omega position, or at the omega-1 position with either R- or S-stereochemistry into saturated or unsaturated MKs, yielding the library of HMK compounds 1-6 (FIG. 3).

HMKs 1-6 are also produced through a second process, which operates independently or simultaneously in the recombinant cells comprising the invention. In Process 2 (FIG. 2), saturated or unsaturated fatty acids are produced endogenously from glucose as described in Process 1 (FIG. 1). In Process 2, these fatty acids are converted to hydroxy fatty acids (HFAs) by overexpression of CYP. Various CYPs incorporate omega-, omega-1(R), or omega-1(S) hydroxyl groups in the fatty acids to give HFAs 7-12 (FIG. 2). HFAs 7-12 are converted to HMKs 1-6 by overproducing the acyl-CoA synthetase FadD, the acyl-CoA oxidase Mlut_11700, the acyl-CoA hydroxylase/dehydrogenase FadB, and the acyl-CoA thioesterase FadM combined with removal of the 3-keto-acyl-CoA thiolase FadA.

In some cases, methyl or ethyl branches adjacent to the hydroxyl group are desired. Branched hydroxy methyl ketones (BHMKs) can be produced from branched fatty acids (BFAs) from one or both of the processes 1 and 2 described above (FIG. 3). Branched fatty acids can be produced by overproducing the acyl-ACP thioesterase 'TesA as well as the 3-keto-acyl-ACP synthase FabH from *B. subtilis*, the BKD pathway from *B. subtilis*, and an exogenous or endogenous supply of branched acyl-CoA precursors. Iso- and anteiso-branched saturated fatty acids can be converted to saturated branched hydroxy methyl ketones (SBHMKs) 13-21 by one or both processes 1 and 2 described above (FIG. 3). Similarly, iso- and anteiso-branched unsaturated fatty acids are converted to unsaturated branched hydroxy methyl ketones (UBHMKs) 22-30 by one or both processes 1 and 2 described above (FIG. 4).

While many of the straight-chain HMKs 1-6 have been described previously, most if not all of the saturated and unsaturated branched HMKs are novel compounds that have not been reported or prepared previously, and so this invention comprises the compositions of SBHMKs 13-21 and the compositions of UBHMKs 22-30 (FIG. 4).

The invention additionally comprises a process for cyclizing HMKs into MCKs. First, the hydroxyl group is derivatized to a reactive leaving group, thus converting the hydroxyl-bound carbon into a electrophile. There are several inexpensive, commercially available chemical reagents for derivatizing hydroxyl groups, including, but not limited to, mesyl chloride and tosyl chloride. Leaving groups are denoted generally as "LG" in FIG. 5. After the hydroxyl group is derivatized to a good leaving group, the compounds are treated with a very strong, sterically hindered base, such as lithium diisopropyl amide (LDA). LDA deprotonates the methyl group adjacent to the ketone and yields an enolate species. The enolate group then displaces the derivatized hydroxyl group through and $S_N2$ nucleophilic attack, creating a C—C bond and yielding a macrocyclic ketone (FIG. 5). Depending on the presence or absence of double bonds in the hydrocarbon chain, and depending on the stereo- and regiospecificity of hydroxylation, HMKs 1-6 are converted to MCKs 31-36 using this process.

Using this same two-step, one-pot chemical process, HMKs 13-21 can be converted to MCKs 37-45 (FIG. 6).

Similarly, unsaturated HMKs 22-30 can be converted to MCKs 46-54 (FIG. 7).

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
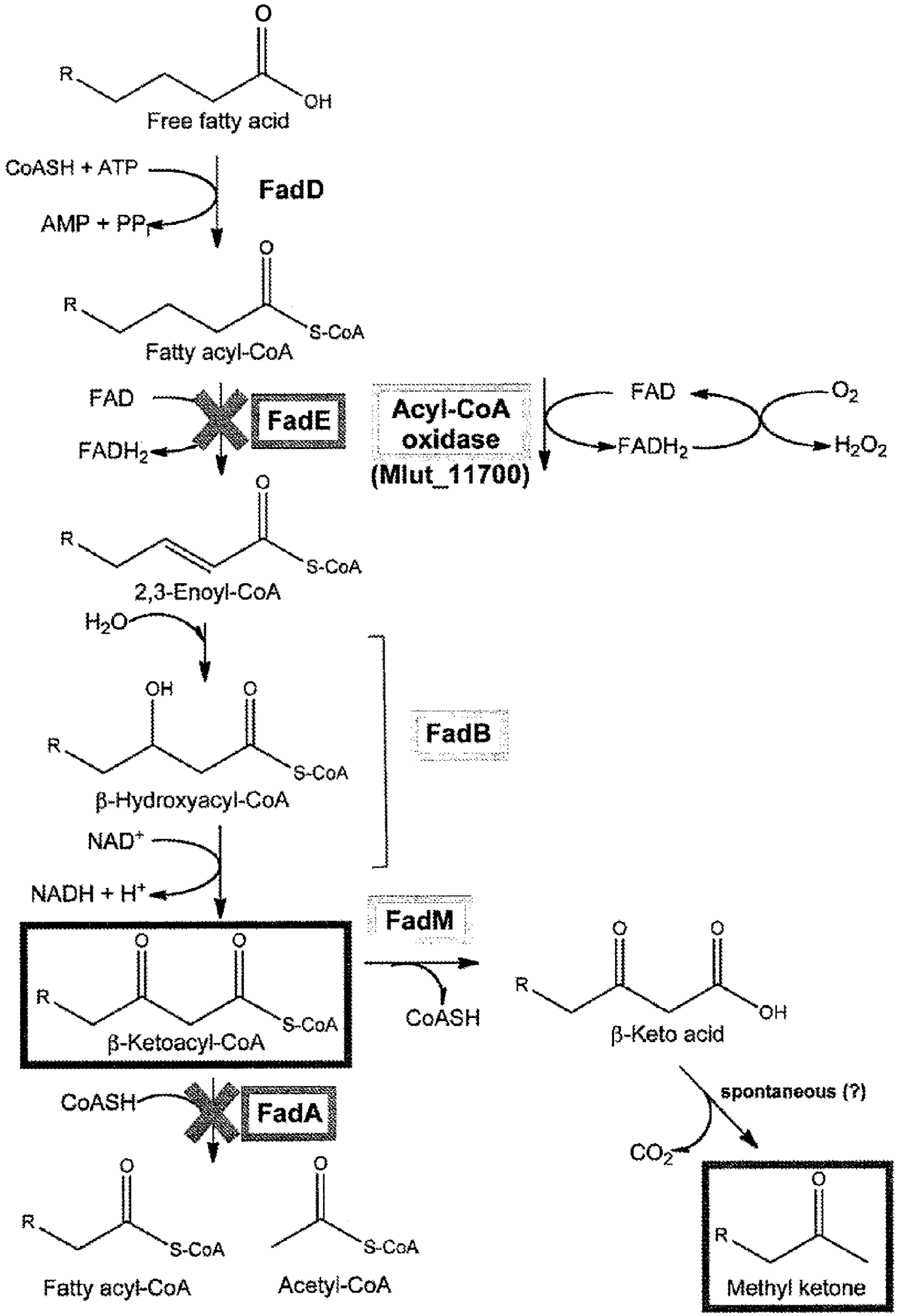
PRIOR ART FIG. 1
FIG. 1 shows a summary of a prior art engineered pathway to convert fatty acids to methyl ketones in *E. coli* DH1 disclosed in U.S. Pat. No. 9,556,458. Green boxes indicate overexpressed genes and red boxes indicate chromosomal deletions. The blue box indicates the putative substrate for FadM (producing free β-keto acids) and the purple box indicates the final methyl ketone product (putatively generated by spontaneous decarboxylation of β-keto acids). The 'TesA thioesterase used for fatty acid overproduction is not depicted in this figure.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" when applied to a value, describes a value that includes up to 10% more than the value described, and up to 10% less than the value described.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "heterologous" means a composition that in nature is not connected or is foreign to another composition. For example, a composition is heterologous to another composition as both are not found in nature in the same cell. For example, an ORF and a promoter can be found in the same cell but are heterologous to each other because one is not operatively linked to the other.

The term "native" means a composition that is connected within a compound, structure or living organism found in nature. For example, a composition is native to another composition as both are found in nature in the same cell. For example, an ORF and a promoter are native to each other if they can be found operatively linked to each other in the same polynucleotide or nucleic acid molecule in nature.

The terms "expression vector" or "vector" refer to a compound and/or composition that transforms, or infects a microbe, thereby causing the cell to express nucleic acids and/or proteins other than those native to the cell, or in a manner not native to the cell. An "expression vector" contains a sequence of nucleic acids (ordinarily RNA or DNA) to be expressed by the microbe. Optionally, the expression vector also comprises materials to aid in achieving entry of the nucleic acid into the microbe, such as a virus, liposome, protein coating, or the like. The expression vectors contemplated for use in the present invention include those into which a nucleic acid sequence can be inserted, along with any preferred or required operational elements. Further, the expression vector must be one that can be transferred into a microbe and replicated therein. In some embodiments, the expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "isolated", "purified", or "biologically pure" refer to material that is substantially or essentially free of components that normally accompany it in its native state or free of components from a yeast cell or culture medium from which the material is obtained.

The term "operably linked" refers to a functional linkage between a nucleic acid expression control sequence (such as a promoter) and a second nucleic acid sequence, wherein the expression control sequence directs transcription of the nucleic acid corresponding to the second sequence, such as an ORF.

The term "yeast" refers to any yeast species including: ascosporogenous yeasts (Endomycetales), basidiosporogenous yeasts and yeast belonging to the Fungi imperfecti (Blastomycetes). The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium* and *Filobasidiella*. Yeast belonging to the Fungi Imperfecti are divided into two families, Sporobolomycetaceae (e.g., genera *Sporobolomyces, Bullera*) and Cryptococcaceae (e.g., genus *Candida*). Of particular interest to the present invention are species within the genera *Pichia, Kluyveromyces, Saccharomyces, Schizosaccharomyces* and *Candida*. Of particular interest are the *Saccharomyces* species *S. cerevisiae, S. carlsbergensis, S. diastaticus, S. douglasii, S. kluyveri, S. norbensis* and *S. oviformis*. Species of particular interest in the genus *Kluyveromyces* include *K. lactis*. Since the classification of yeast may change in the future, for the purposes of this invention, yeast shall be defined as described in Biology and Activities of Yeast (F. A. Skinner, S. M. Passmore & R. R. Davenport eds. 1980) (Soc. App. Bacteriol. Symp. Series No. 9). In addition to the foregoing, those of ordinary skill in the art are presumably familiar with the biology of yeast and the manipulation of yeast genetics. See, e.g., Biochemistry and Genetics of Yeast (M. Bacila, B. L. Horecker & A. O. M. Stoppani eds. 1978); The Yeasts (A. H. Rose & J. S. Harrison eds., 2nd ed., 1987); The Molecular Biology of the Yeast *Saccharomyces* (Strathern et al. eds.

Enzymes, and Nucleic Acids Encoding Thereof

A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the Lad repressor protein from binding to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

When the host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of the HMK is ensured. When added, any intermediate is present in an excess amount in the culture medium.

Any means for extracting or separating the HMK from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

Host Cells

In some embodiments, the host cells are genetically modified in that heterologous nucleic acid have been introduced into the host cells, and as such the genetically modified host cells do not occur in nature. The suitable host cell is one capable of expressing a nucleic acid construct encoding one or more enzymes described herein. The gene (s) encoding the enzyme(s) may be heterologous to the host cell or the gene may be native to the host cell but is operatively linked to a heterologous promoter and one or more control regions which result in a higher expression of the gene in the host cell.

Each introduced enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

The genetically modified host cell can be any bacterial cell capable of production of HMK in accordance with the methods of the invention.

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Generally, although not necessarily, the microbe is a yeast or a bacterium. In some embodiments, the microbe is *Rhodosporidium toruloides* or *Pseudomonas putida*. In some embodiments, the microbe is a Gram negative bacterium. In some embodiments, the microbe is of the phylum Proteobactera. In some embodiments, the microbe is of the class Gammaproteobacteria. In some embodiments, the microbe is of the order Enterobacteriales. In some embodiments, the microbe is of the family Enterobacteriaceae. Examples of suitable bacteria include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus* taxonomical classes. Suitable eukaryotic microbes include, but are not limited to, fungal cells. Suitable fungal cells are yeast cells, such as yeast cells of the *Saccharomyces* genus.

Yeasts suitable for the invention include, but are not limited to, *Yarrowia, Candida, Bebaromyces, Saccharomyces, Schizosaccharomyces* and *Pichia* cells. In some embodiments, the yeast is *Saccharomyces cerevisae*. In some embodiments, the yeast is a species of *Candida*, including but not limited to *C. tropicalis, C. maltosa, C. apicola, C. paratropicalis, C. albicans, C. cloacae, C. guilliermondii, C. intermedia, C. lipolytica, C. parapsilosis* and *C. zeylenoides*. In some embodiments, the yeast is *Candida tropicalis*. In some embodiments, the yeast is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast is an oleaginous yeast. In some embodiments, the oleaginous yeast is a *Rhodosporidium* species. In some embodiments, the *Rhodosporidium* species is *Rhodosporidium toruloides.*

In some embodiments, the host cell is a prokaryotic cell, such as a bacterial cell. In some embodiments, the host cell is a bacterial cell selected from the *Escherichia, Enterobacter, Azotobacter, Erwinia, Bacillus, Pseudomonas, Klebsiella, Proteus, Salmonella, Serratia, Shigella, Ralstonia, Rhizobia*, or *Vitreoscilla* taxonomical class. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtherias, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium uropygiale*. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or *S. scabies*. In some embodiments, the *Bacillus* cell is a *B. subtilis, B. megaterium, B. licheniformis, B. anthracis, B. amyloliquefaciens, B. pumilus, B. brevis, B. aminovorans*, or *B. fusiformis*.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Host Cell Genetically Modified to Produce Hydroxylated Methyl Ketones (HMK)

The invention comprises novel processes for producing, and recombinant cells that produce, hydroxylated methyl ketones (HMKs) from glucose, as well as the compositions of several novel compounds and the process for converting these HMKs into macrocyclic ketones (MCKs), many of which are high value fragrance compounds. The invention provides a means of producing several previously uncharacterized compounds that are structurally related to high value fragrance molecules and could be investigated as novel fragrance compounds.

Figure 2:
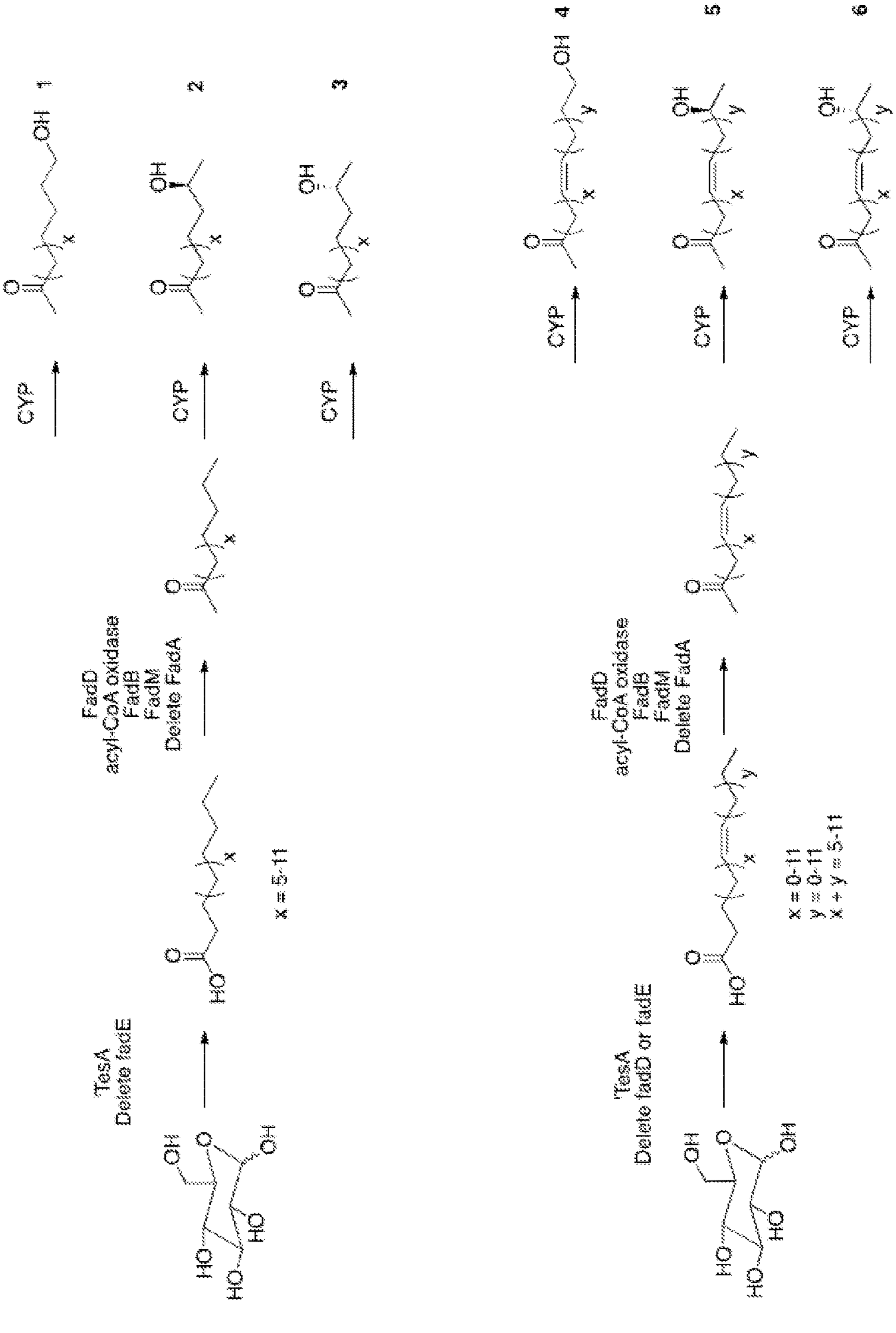
FIG. 2 shows an enzymatic pathway for converting glucose into a saturated or unsaturated hydroxylated methyl ketone (HMK), specifically HMK compounds 1-6. For compounds 1, 2, and 3: x is 5, 6, 7, 8, 9, 10, or 11. For compounds 4, 5, or 6: x is 0, 1, 2, 3, 4, 5, 6, 7, 8, 9, 10, or 11; y is 0, 1, 2, 3, 4, 5, 6, 7, 8, 9, 10, or 11; x+y is 5, 6, 7, 8, 9, 10, or 11.

The recombinant cells that produce HMKs do so through either one of the following, or both of the following processes: In Process 1, the cells produce free fatty acids by overproducing the acyl-ACP thioesterase 'TesA and removing the enzyme FadE, which participates in the degradation of fatty acids. The fatty acids produced are a combination of saturated and unsaturated fatty acids (FIG. 2). These free fatty acids are converted to methyl ketones (MKs) by overproducing the acyl-CoA synthetase FadD, the acyl-CoA oxidase Mlut_11700, the acyl-CoA hydroxylase/dehydrogenase FadB, and the acyl-CoA thioesterase FadM combined with removal of the 3-keto-acyl-CoA thiolase FadA. In process 1, endogenously produced MKs are subsequently converted to HMKs by overproducing a bacterial cytochrome P450 (CYP) enzyme. Different CYP enzymes can install hydroxyl groups at the omega position, or at the omega-1 position with either R- or S-stereochemistry into saturated or unsaturated MKs, yielding the library of HMK compounds 1-6 (FIG. 2).

Figure 3:
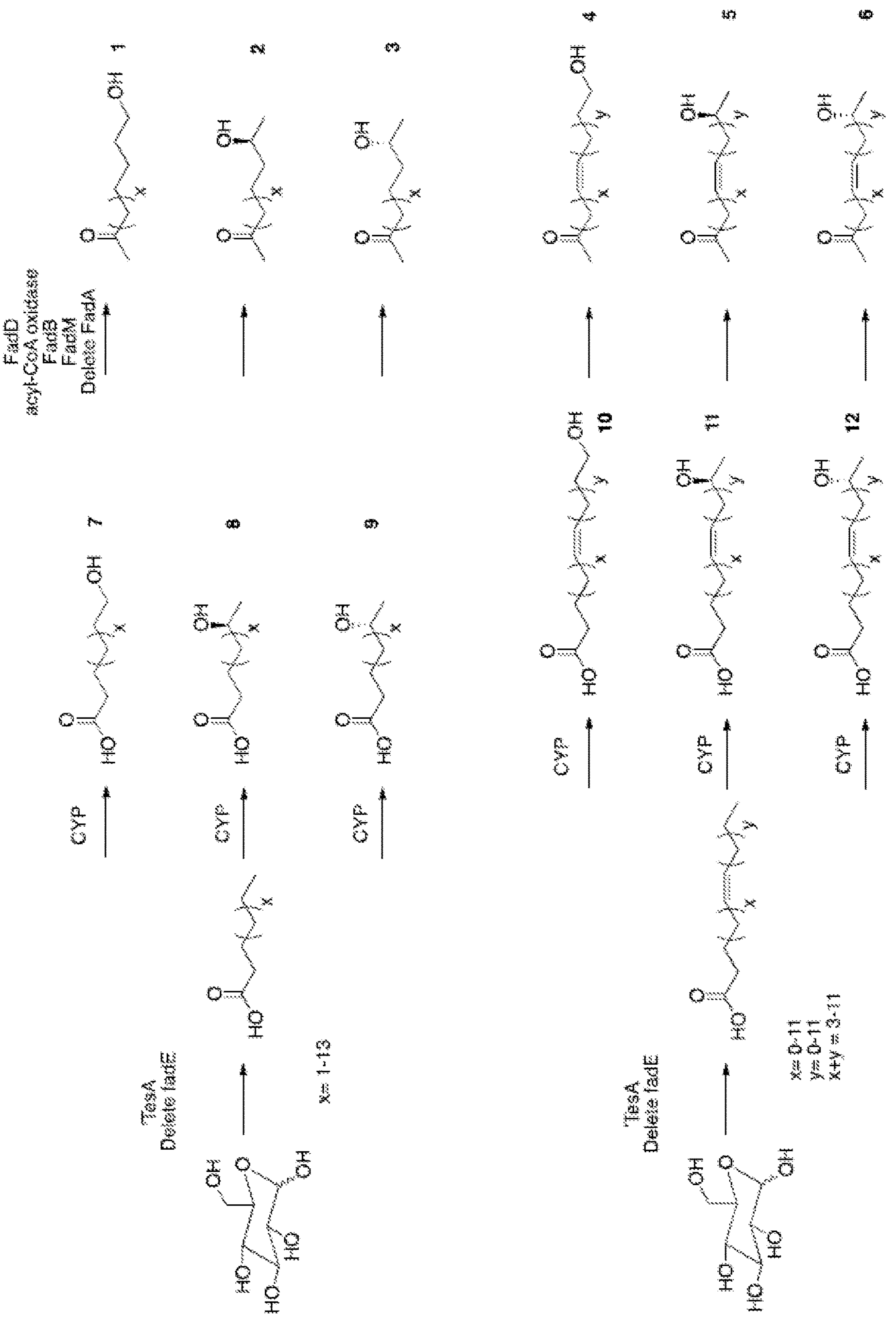
FIG. 3 shows an alternate enzymatic pathway for converting glucose into a saturated or unsaturated hydroxylated methyl ketone (HMK), specifically HMK compounds 1-6. For compounds 1, 2, 3, 7, 8, and 9: x is 1, 2, 3, 4, 5, 6, 7, 8, 9, 10, 11, 12, or 13. For compounds 4, 5, 6, 10, 11, and 12: x is 0, 1, 2, 3, 4, 5, 6, 7, 8, 9, 10, or 11; y is 0, 1, 2, 3, 4, 5, 6, 7, 8, 9, 10, or 11; x+y is 3, 4, 5, 6, 7, 8, 9, 10, or 11.

HMKs 1-6 are also produced through a second process, which operates independently or simultaneously in the recombinant cells comprising the invention. In Process 2 (FIG. 3), saturated or unsaturated fatty acids are produced endogenously from glucose as described in Process 1 (FIG. 2). In Process 2, these fatty acids are converted to hydroxy fatty acids (HFAs) by overexpression of CYP. Various CYPs incorporate omega-, omega-1(R), or omega-1(S) hydroxyl groups in the fatty acids to give HFAs 7-12 (FIG. 3). HFAs 7-12 are converted to HMKs 1-6 by overproducing the acyl-CoA synthetase FadD, the acyl-CoA oxidase Mlut_11700, the acyl-CoA hydroxylase/dehydrogenase FadB, and the acyl-CoA thioesterase FadM combined with removal of the 3-keto-acyl-CoA thiolase FadA.

In some cases, methyl or ethyl branches adjacent to the hydroxyl group are desired. Branched hydroxy methyl ketones (BHMKs) can be produced from branched fatty acids (BFAs) from one or both of the processes 1 and 2 described above (FIG. 4). Branched fatty acids can be produced by overproducing the acyl-ACP thioesterase 'TesA as well as the 3-keto-acyl-ACP synthase FabH from *B. subtilis*, the BKD pathway from *B. subtilis*, and an exogenous or endogenous supply of branched acyl-CoA precursors. Iso- and anteiso-branched saturated fatty acids can be converted to saturated branched hydroxy methyl ketones (SBHMKs) 13-21 by one or both processes 1 and 2 described above (FIG. 4). Similarly, iso- and anteiso-branched unsaturated fatty acids are converted to unsaturated branched hydroxy methyl ketones (UBHMKs) 22-30 by one or both processes 1 and 2 described above (FIG. 4).

Figure 4:
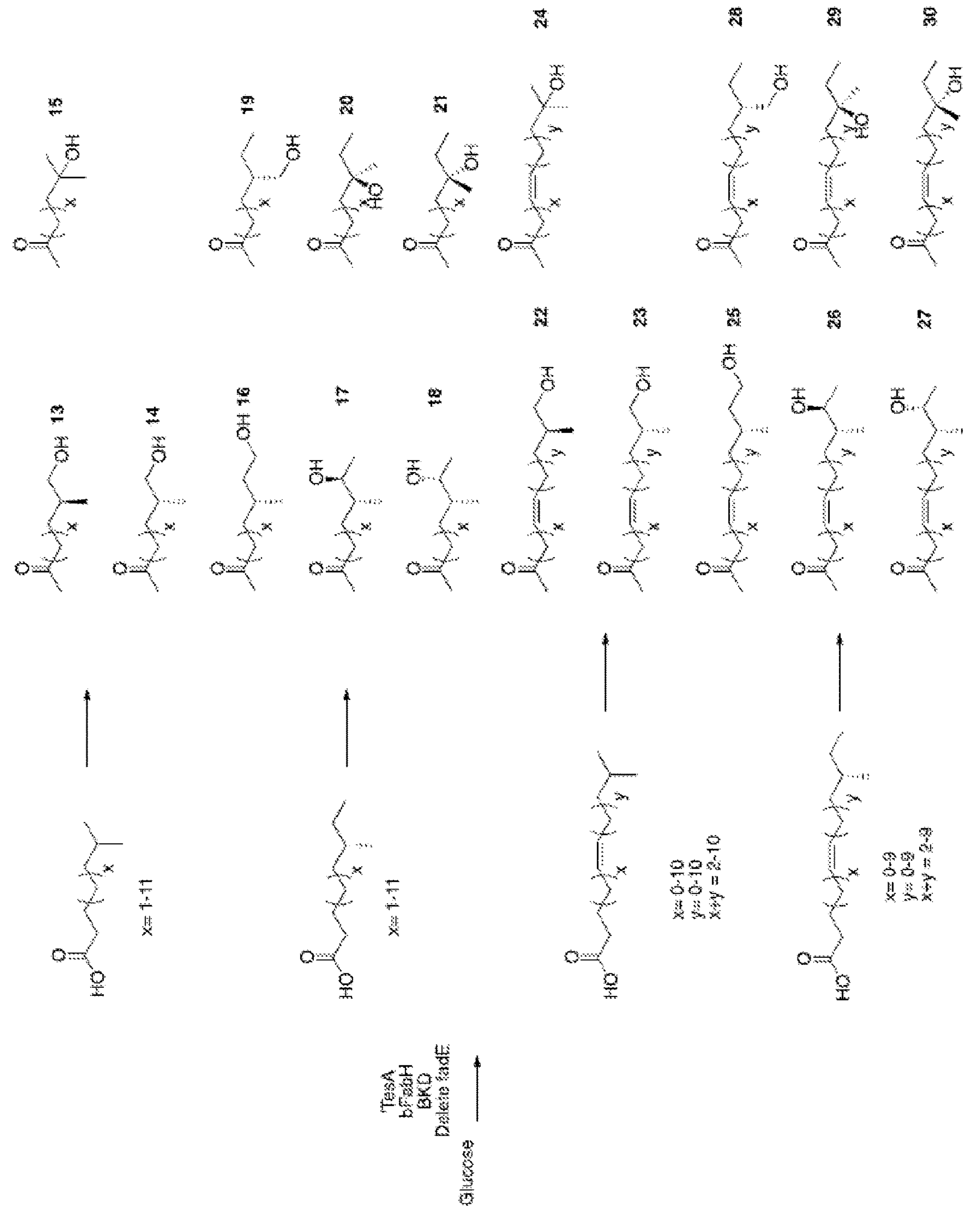
FIG. 4 shows an enzymatic pathway for converting glucose into a saturated branched hydroxy methyl ketone (SBHMK), specifically SBHMK compounds 13-21, and an unsaturated branched hydroxy methyl ketone (UBHMK), specifically UBHMK compounds 22-30. For compounds 13-21: x is 1, 2, 3, 4, 5, 6, 7, 8, 9, 10, or 11. For compounds 22-30: x is 0, 1, 2, 3, 4, 5, 6, 7, 8, 9, or 10; y is 0, 1, 2, 3, 4, 5, 6, 7, 8, 9, or 10; x+y is 2, 3, 4, 5, 6, 7, 8, or 9.

While many of the straight-chain HMKs 1-6 have been described previously, most if not all of the saturated and unsaturated branched HMKs are novel compounds that have not been reported or prepared previously, and so this invention comprises the compositions of SBHMKs 13-21 and the compositions of UBHMKs 22-30 (FIG. 4).

Figure 5:
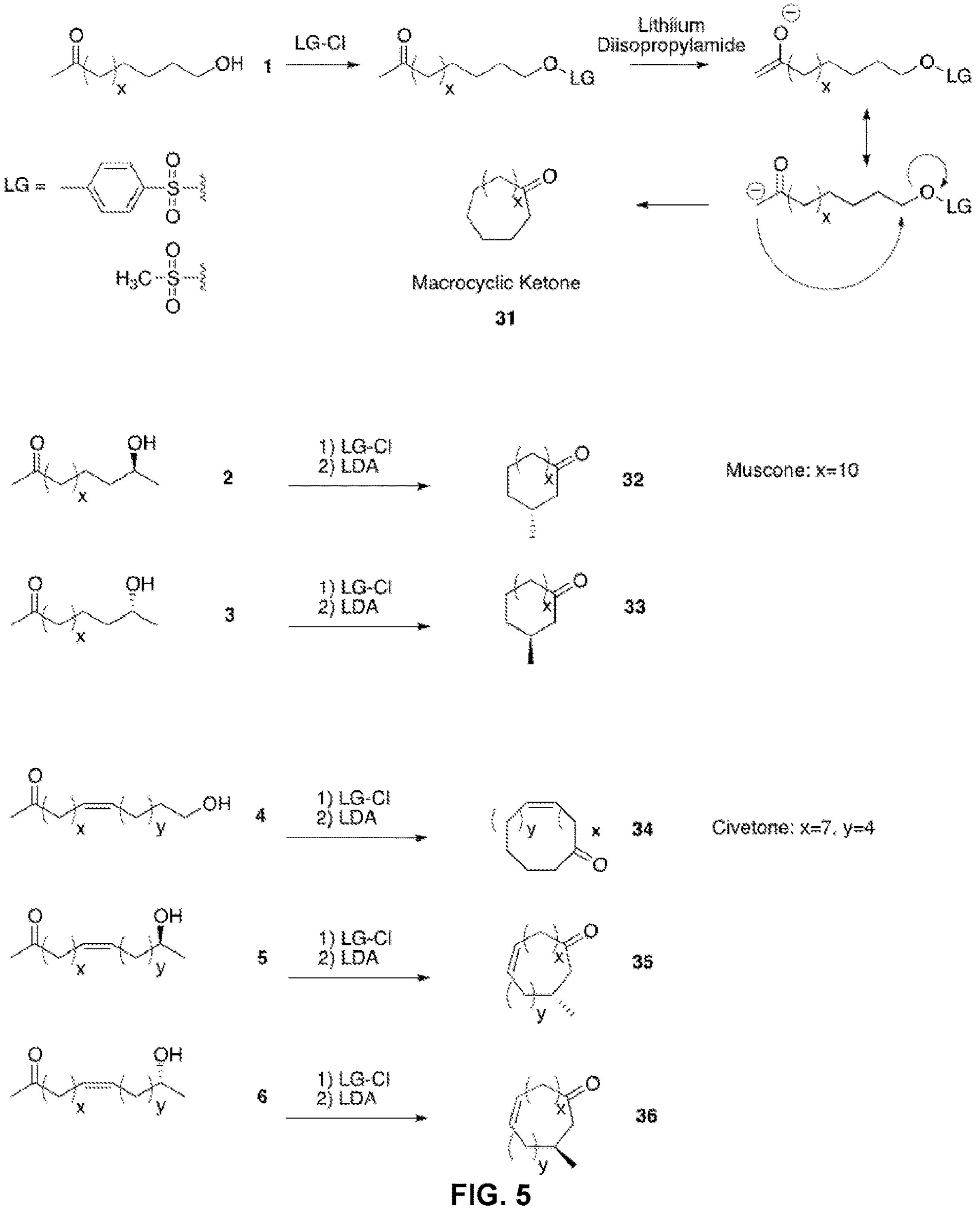
FIG. 5 shows the conversion of HMK compounds 1-6 into macrocyclic ketone (MCK) compounds 31-36.

The invention additionally comprises a process for cyclizing HMKs into MCKs. First, the hydroxyl group is derivatized to a reactive leaving group, thus converting the hydroxyl-bound carbon into a electrophile. There are several inexpensive, commercially available chemical reagents for derivatizing hydroxyl groups, including, but not limited to, mesyl chloride and tosyl chloride. Leaving groups are denoted generally as "LG" in FIG. 5. After the hydroxyl group is derivatized to a good leaving group, the compounds are treated with a very strong, sterically hindered base, such as lithium diisopropyl amide (LDA). LDA deprotonates the methyl group adjacent to the ketone and yields an enolate species. The enolate group then displaces the derivatized hydroxyl group through and $S_N2$ nucleophilic attack, creating a C—C bond and yielding a macrocyclic ketone (FIG. 5). Depending on the presence or absence of double bonds in the hydrocarbon chain, and depending on the stereo- and regiospecificity of hydroxylation, HMKs 1-6 are converted to MCKs 31-36 using this process.

Figure 6:
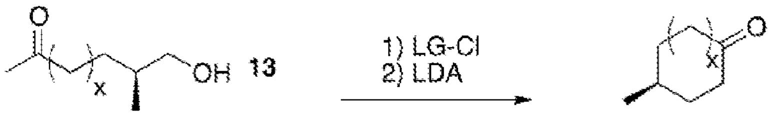
FIG. 6 shows the conversion of SBHMK compounds 13-21 into macrocyclic ketone (MCK) compounds 37-45.
Figure 6:
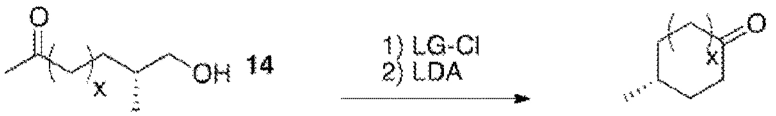
Figure 6:
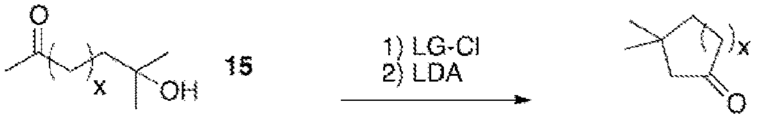
Figure 6:
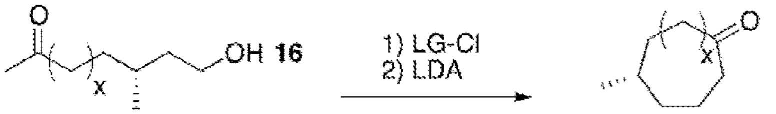
Figure 6:
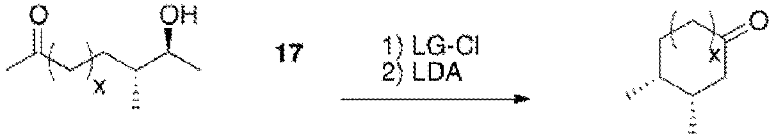
Figure 6:
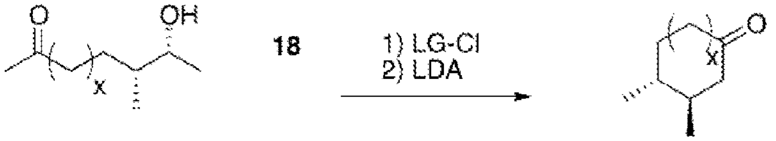
Figure 6:
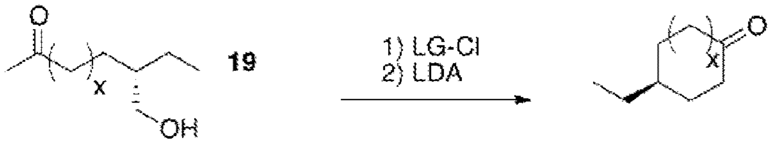
Figure 6:
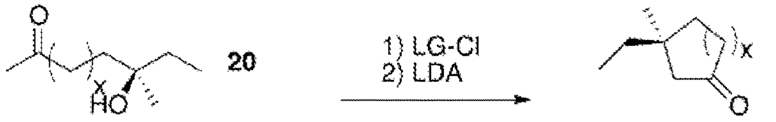
Figure 6:
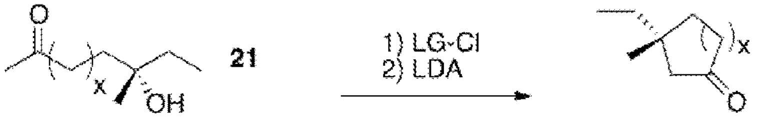

Using this same two-step, one-pot chemical process, HMKs 13-21 can be converted to MCKs 37-45 (FIG. 6).

Figure 7:
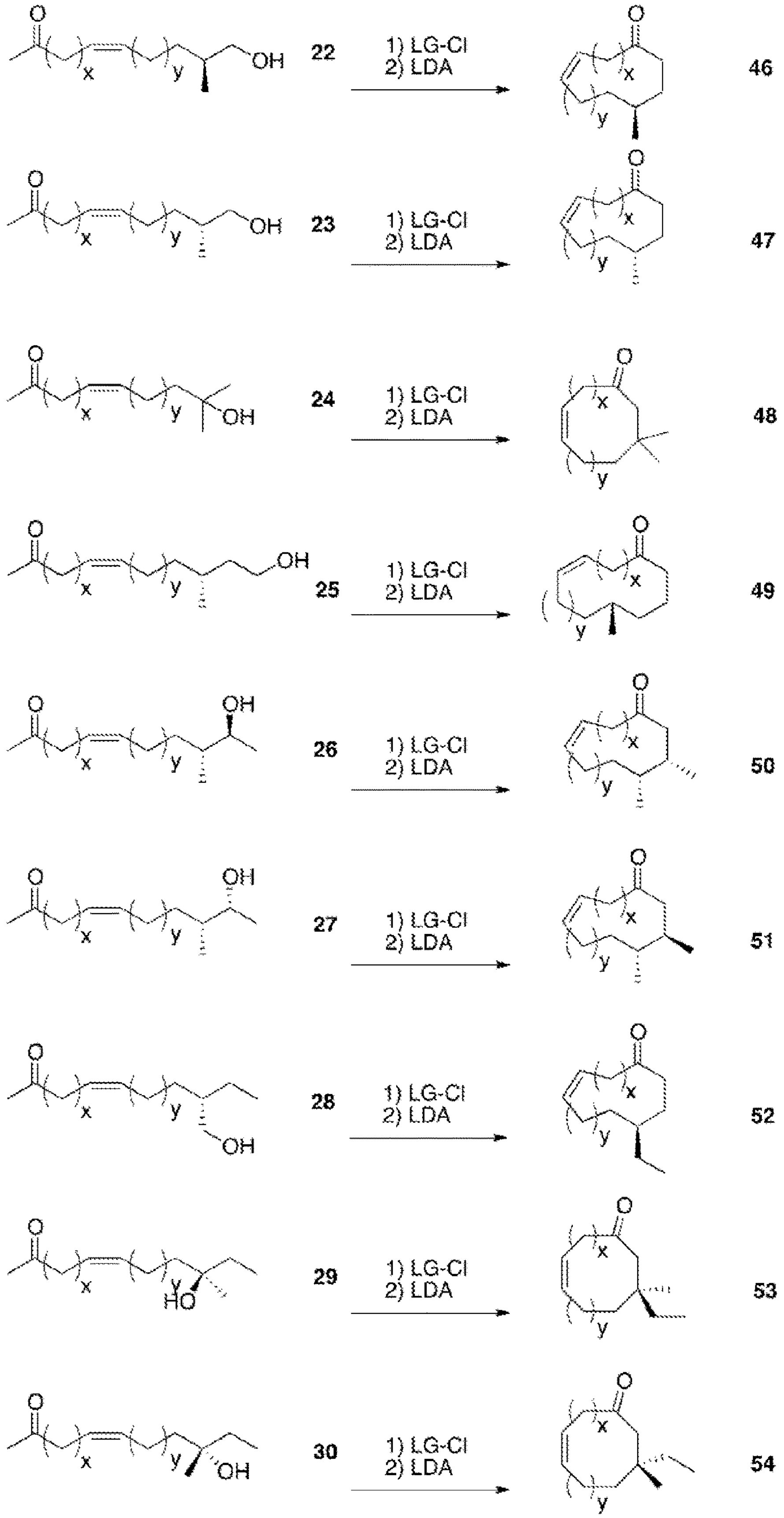
FIG. 7 shows the conversion of HMK compounds 22-30 into macrocyclic ketone (MCK) compounds 46-54.

Similarly, unsaturated HMKs 22-30 can be converted to MCKs 46-54 (FIG. 7).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell capable of producing or overproducing a hydroxylated methyl ketone (HMK) comprising: (a) a recombinant nucleic acid construct encoding a bacterial cytochrome P450 (CYP) enzyme that is capable of incorporating an omega-, omega-1(R), or omega-1(S) hydroxyl group in a fatty acids to convert a fatty to a hydroxy fatty acid (HFA), and overproduces fatty acid compared to a control host cell that has not been transformed with the nucleic acid construct encoding the bacterial CYP enzyme, (b) a recombinant nucleic acid construct encoding a FadM that is capable of converting a β-ketoacyl-CoA to a β-keto acid, and overproduces β-ketoacyl-CoAs compared to a control bacterial host cell that has not been transformed with the nucleic acid construct encoding the FadM, wherein the FadM comprises an amino acid sequence having at least 90% identity to SEQ ID NO:1; (c) a recombinant nucleic acid sequence that encodes an acyl-CoA oxidase capable of converting an acyl-CoA to a trans-2-enoyl-CoA; (d) a recombinant nucleic acid sequence that encodes a FadB capable of converting a trans-2-enoyl-CoA to a β-hydroxyacyl-CoA and a β-hydroxyacyl-CoA to a β-ketoacyl-CoA; and (e) has an inactive fadA gene or chromosomal deletion of all or part of a fadA gene such that the host cell does not express active 3-keto-acyl-CoA thiolase (FadA); wherein the fatty acid is

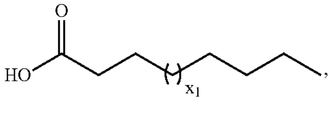

, wherein $x_1$ is 5-11,

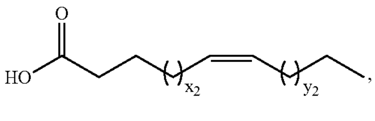

, wherein $x_2$ is 0-11, $y_2$ is 0-11, and $x_2+y_2$ is 5-11,

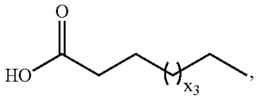

, wherein $x_3$ is 1-13,

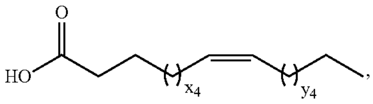

, wherein $x_4$ is 0-11, $y_4$ is 0-11, and $x_4+y_4$ is 3-11,

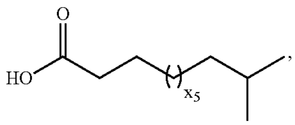

, wherein $x_5$ is 1-11,

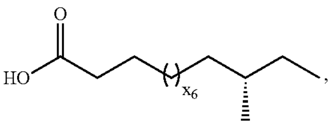

, wherein $x_6$ is 1-11,

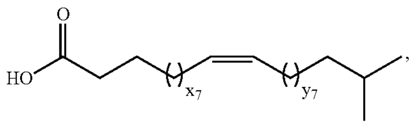

wherein $x_7$ is 0-10, $y_7$ is 0-10, and $x_7+y_7$ is 2-10, or

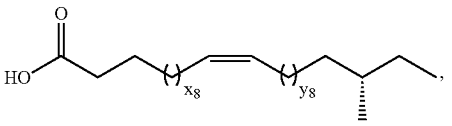

wherein $x_8$ is 0-9, $y_8$ is 0-9, and $x_8+y_8$ is 2-9.

2. The genetically modified host cell of claim 1, wherein the HMK is an omega-hydroxy methyl ketone or omega-1-hydroxy methyl ketone.

3. The genetically modified host cell of claim 1, wherein the HMK is a branched HMK (BHMK).

4. The genetically modified host cell of claim 3, wherein the HMK is a saturated branched HMK (SBHMK).

5. The genetically modified host cell of claim 3, wherein the HMK is an unsaturated branched HMK (UBHMK).

6. The genetically modified host cell of claim 1, wherein the HMK is a saturated HMK (SHMK) or unsaturated HMK (UHMK).

7. The genetically modified host cell of claim 1, wherein the genetically modified host cell further comprises a recombinant nucleic acid sequence that encodes a cytoplasmically-directed thioesterase.

8. The genetically modified host cell of claim 1, wherein the genetically modified host cell has an inactive fadE gene or chromosomal deletion of all or part of a fadE gene such that the host cell does not express active FadE.

9. The genetically modified host cell of claim 1, wherein the FadM comprises an amino acid sequence having at least 95% identity to SEQ ID NO:1.

10. The genetically modified host cell of claim 9, wherein the FadM comprises an amino acid sequence having at least 99% identity to SEQ ID NO:1.

11. The genetically modified host cell of claim 10, wherein the FadM comprises an amino acid sequence having 100% identity to SEQ ID NO:1.

12. The genetically modified host cell of claim 1, wherein the fatty acid is

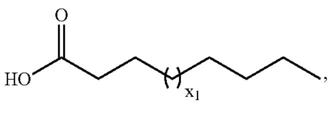

wherein $x_1$ is 5-11.

13. The genetically modified host cell of claim 1, the fatty acid is

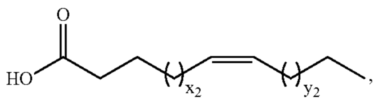

wherein $x_2$ is 0-11, $y_2$ is 0-11, and $x_2+y_2$ is 5-11.

14. The genetically modified host cell of claim 1, the fatty acid is

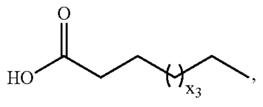

wherein $x_3$ is 1-13.

15. The genetically modified host cell of claim 1, the fatty acid is

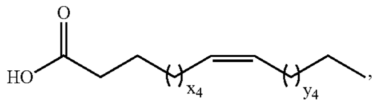

wherein $x_4$ is 0-11, $y_4$ is 0-11, and $x_4+y_4$ is 3-11.

16. The genetically modified host cell of claim 1, the fatty acid is

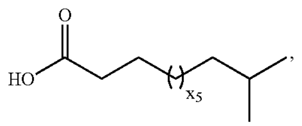

wherein $x_5$ is 1-11.

17. The genetically modified host cell of claim 1, the fatty acid is

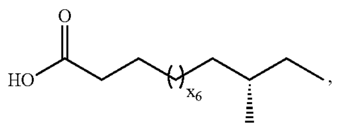

wherein $x_6$ is 1-11.

18. The genetically modified host cell of claim 1, the fatty acid is

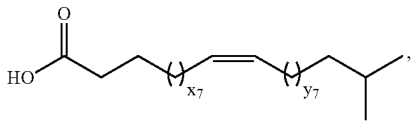

wherein $x_7$ is 0-10, $y_7$ is 0-10, and $x_7+y_7$ is 2-10.

19. The genetically modified host cell of claim 1, the fatty acid is

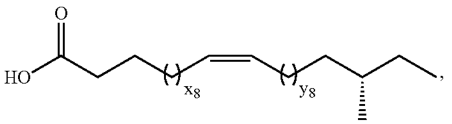

wherein $x_8$ is 0-9, $y_8$ is 0-9, and $x_8+y_8$ is 2-9.

20. A method of enhancing production of methyl ketones, the method comprising: culturing the genetically modified host cell of claim 1 under conditions such that the culturing results in the production of HMK.

21. The method of claim 20, wherein the method further comprises recovering the HMK.

22. The method of claim 21, wherein the recovering step uses a decane overlay to recover the HMK.

23. The method of claim 20, wherein the HMK is an omega-hydroxy or omega-1-hydroxy methyl ketone.

* * * * *